United States Patent [19]

Fuchs et al.

[11] 4,140,768

[45] Feb. 20, 1979

[54] O-ALKYL-O-[6-SUBSTITUTED-PYRIDAZIN(-3)YL]-(THIONO)(THIOL)ALKANEPHOSPHONIC ACID ESTERS FOR COMBATING PESTS

[75] Inventors: Rainer A. Fuchs; Fritz Maurer; Hans-Jochem Riebel; Rolf Schröder, all of Wuppertal; Ingeborg Hammann, Cologne; Wolfgang Behrenz, Overath-Steinenbrueck; Bernhard Homeyer, Leverkusen, all of Fed. Rep. of Germany

[73] Assignee: Bayer Aktiengesellschaft, Leverkusen, Fed. Rep. of Germany

[21] Appl. No.: 713,741

[22] Filed: Aug. 11, 1976

[30] Foreign Application Priority Data

Aug. 21, 1975 [DE] Fed. Rep. of Germany ....... 2537353

[51] Int. Cl.$^2$ .......................... A01N 9/38; C07F 9/65
[52] U.S. Cl. ........................... 424/200; 544/232
[58] Field of Search ............ 260/250 A; 424/200; 544/232

[56] References Cited

U.S. PATENT DOCUMENTS 3,950,334  4/1976  Riebel .......................... 260/250 AP

FOREIGN PATENT DOCUMENTS 2049813  4/1972  Fed. Rep. of Germany.
38/26389  12/1973  Japan ........................... 260/250 AP

OTHER PUBLICATIONS

FBA, Chem. Abs., 73, 14998(a), 1970.
Taketa I, Chem. Abs. 60, 6869f (1963).

*Primary Examiner*—Mark L. Berch
*Attorney, Agent, or Firm*—Sprung, Felfe, Horn, Lynch & Kramer

[57] ABSTRACT

O-Alkyl-O-[6-substituted pyridazin(3)yl]-thiono)(thiol-)alkanephosphonic acid esters of the formula

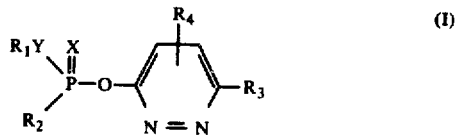

in which
  X and Y each independently is oxygen or sulfur,
  $R_1$ is alkyl with 1 to 6 carbon atoms,
  $R_2$ is alkyl with 1 to 4 carbon atoms,
  $R_3$ is alkoxy with 1 to 4 carbon atoms, alkynyloxy with 2 to 5 carbon atoms, alkylsulfonyloxy with 1 to 3 carbon atoms, monoalkylcarbamoyloxy with 1 to 3 carbon atoms, halogen, benzyloxy, benzoyloxy, phenoxy, or phenoxy carrying at least one substituent selected from halogen, nitro, cyano, —SO$_2$CH$_3$, —SO$_2$CH$_2$Cl, and alkyl, halogenalkyl or alkylthio, each with up to 3 carbon atoms, and
  $R_4$ is hydrogen or alkyl with 1 to 3 carbon atoms, which possess insecticidal, acaricidal, nematicidal and fungicidal properties.

10 Claims, No Drawings

O-ALKYL-O-[6-SUBSTITUTED-PYRIDAZIN(3)YL]-(THIONO) (THIOL)ALKANEPHOSPHONIC ACID ESTERS FOR COMBATING PESTS

The present invention relates to and has for its objects the provision of particular new substituted O-alkyl-O-[6-substituted-pyridazin(3)yl]-(thiono) (thiol)alkanephosphonic acid esters which possess insecticidal, acaricidal, nematicidal and fungicidal properties, active compositions in the form of mixtures of such compounds with solid and liquid dispersible carrier vehicles, and methods for producing such compounds and for using such compounds in a new way especially for combating pests, e.g. insects, acarids, nematodes and fungi, with other and further objects becoming apparent from a study of the within specification and accompanying examples.

It is known from U.S. Pat. No. 2,759,938 and German Published Specification Dos No. 2,049,813 that substituted pyridazinylthionophosphoric(phosphonic)acid esters, for example, O,O-diethyl-O-[6-hydroxy-(Compound A) or 6-chloro- (Compound B) or 6-N,N-dimethylcarbamoyloxy-pyridazin(3)yl]-thionophosphoric acid ester (Compound C), and from published Netherlands Patent application No. 6,904,664 O-ethyl-O-[1,6-dihydro-6-oxo-pyridazin(3)yl]-thionomethane-(Compound D) and ethanephosphonic acid ester (Compound E), have insecticidal and acaricidal properties.

The present invention provides, as new compounds, the pyridazinyl(thiono) (thiol)phosphonic acid esters of the general formula $$R_1Y\underset{R_2}{\overset{X}{\underset{\|}{\diagdown}}}P-O-\underset{N=N}{\overset{R_4}{\diagup\!\!\!\diagdown}}-R_3 \quad (I)$$

in which
X and Y each independently is oxygen or sulfur,
$R_1$ is alkyl with 1 to 6 carbon atoms,
$R_2$ is alkyl with 1 to 4 carbon atoms,
$R_3$ is alkoxy with 1 to 4 carbon atoms, alkynyloxy with 2 to 5 carbon atoms, alkylsulfonyloxy with 1 to 3 carbon atoms, monoalkylcarbamoyloxy with 1 to 3 carbon atoms, halogen, benzyloxy, benzoyloxy, phenoxy, or phenoxy carrying at least one substituent selected from halogen, nitro, cyano, $-SO_2CH_3$, $-SO_2CH_2Cl$, and alkyl, halogenalkyl or alkylthio, each with up to 3 carbon atoms, and
$R_4$ is hydrogen or alkyl with 1 to 3 carbon atoms.

Preferably, X represents sulfur, Y represents oxygen, $R_1$ represents straight-chain or branched alkyl with 1 to 5 carbon atoms, $R_2$ represents straight-chain or branched alkoxy with 1 to 3 carbon atoms, straight-chain or branched alkynyloxy with 3 or 4 carbon atoms, chlorine, bromine, methylsulfonyloxy, ethylsulfonyloxy, N-methyl-carbamoyloxy or N-ethylcarbamoyloxy, benzoyloxy or benzyloxy or represents phenyloxy which preferably carries one, two or three substituents selected from chlorine, nitro, cyano, methyl, ethyl, methylthio, ethylthio and trifluoromethyl, the substituents not necessarily being identical in the case of di- or trisubstitution, and $R_4$ represents hydrogen, methyl or ethyl.

Surprisingly, the pyridazinyl(thiono)(thiol)phosphonic acid esters according to the invention show a better insecticidal, acaricidal and nematicidal action than the corresponding known substituted pyridazinylthionophosphoric(phosphonic) acid esters of analogous structure and of the same type of action. The products according to the present invention thus represent a genuine enrichment of the art.

The present invention also provides a process for the preparation of a pyridazinyl(thiono)(thiol)phosphonic acid ester of the formula (I) in which (a) a (thiono)(thiol)phosphonic acid ester halide of the general formula $$R_1Y\underset{R_2}{\overset{X}{\underset{\|}{\diagdown}}}P-Hal \quad (II),$$

in which
$R_1$, $R_2$, X and Y have the above-mentioned meanings and
Hal represents halogen, preferably chlorine, is reacted with a 1,6dihydro-6-oxo-pyridazine derivative of the general formula $$R_3-\underset{\underset{H}{N-N}}{\overset{R_4}{\diagup\!\!\!\diagdown}}=O \quad (III),$$

in which
$R_3$ and $R_4$ have the above-mentioned meaning, if appropriate in the presence of an acid acceptor or, if appropriate in the form of a corresponding alkali metal salt, alkaline earth metal salt or ammonium salt, and optionally in the presence of a solvent, or (b) provided that a compound of the formula (I) in which $R_3$ represents alkylsulfonyloxy or benzoyloxy is required, a pyridazinyl (thiono)(thiol)phosphonic acid ester of the general formula $$HO-\underset{N=N}{\overset{R_4}{\diagup\!\!\!\diagdown}}-O-\underset{R_2}{\overset{X}{\underset{\|}{P}}}\diagdown YR_1 \quad (IV),$$

in which
$R_1$, $R_2$, $R_4$, X and Y have the above-mentioned meanings, is reacted with an acyl halide of the general formula $$R_5Hal_2 \quad (V),$$

in which
$R_5$ represents alkylsulfonyl with 1 to 3 carbon atoms or benzoyl, and
$Hal_2$ represents halogen, preferably chlorine,
if appropriate in the presence of an acid acceptor and, if appropriate, in the presence of a solvent, or (c) provided that a compound of the formula (I) in which $R_3$ represents monoalkylcarbamoyloxy is required, a compound of the formula (IV) is reacted with an alkyl isocyanate of the general formula $$Alk-NCO \quad (VI),$$

in which

Alk represents alkyl with 1 to 3 carbon atoms, if appropriate in the presence of a catalyst and, if appropriate, in the presence of a solvent.

If, for example, following process variant (a), S-ethyl-thiolethanephosphonic acid chloride and 3-hydroxy-6-N-ethylcarbamoyloxypyridazine are used, or following process variant (b), O-ethyl-O-[6-hydroxy-pyridazin(-3)yl]-n-propanephosphonic acid diester and benzoyl chloride are used, or following process variant (c), O-ethyl-O-[6-hydroxy-pyridazin(3)yl]-thionoethanephosphonic acid ester and ethyl isocyanate are used as the starting materials, the course of the reaction can be represented by the following equations:

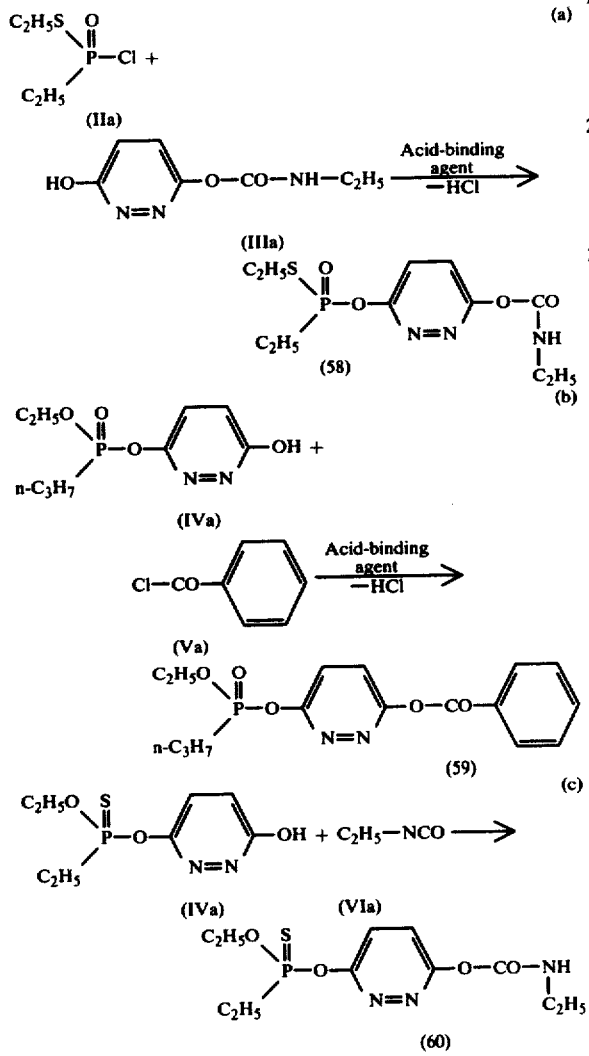

The (thiono)(thiol)phosphonic acid ester halides (II) and pyridazinyl(thiono)thiol)phosphonic acid esters (IV) to be used as starting materials are known and can be prepared in accordance with customary processes (see, for example, U.S. Pat. No. 3,167,574, Belgian Pat. No. 671,913 and Netherlands Pat. Application 6,904,664).

The following may be mentioned as specific examples: O-methyl-, O-ethyl-, O-n-propyl-, O-isopropyl-, O-n-butyl-, O-isobutyl-, O-sec.-butyl-, O-tert.-butyl- and O-n-pentylmethane-, ethane-, n-propane- and isopropane-phosphonic acid ester chlorides and the corresponding thiono analogues; S-methyl-, S-ethyl-, S-n-propyl-, S-isopropyl-, S-n-butyl-, S-isobutyl-, S-sec.-butyl-, S-tert.-butyl- and S-n-pentylmethane-, ethane-, n-propane- and isopropane-thiolphosphonic acid ester chlorides and the corresponding thiono analogues; O-methyl-, O-ethyl-, O-n-propyl-, O-isopropyl-, O-n-butyl-, O-isobutyl-, O-sec.-butyl-, O-tert.-butyl- and O-n-pentyl-O-[4- or 5-methyl-6-hydroxypyridazin(-3)yl]-methane-, ethane-, n-propane- and isopropane-phosphonic acid esters and the corresponding thiono analogues; O-methyl-, O-ethyl-, O-n-propyl-, O-isopropyl-, O-n-butyl-, O-isobutyl-, O-sec.-butyl-, O-tert.-butyl- and O-n-pentyl-O-[6-hydroxypyridazin(3)yl]-methane-, ethane-, n-propane- and isopropane-phosphonic acid esters and the corresponding thiono analogues; and S-methyl-, S-ethyl-, S-n-propyl-, S-isopropyl-, S-n-butyl-, S-isobutyl-, S-sec.-butyl-, S-tert.-butyl- and S-n-pentyl-O-[6-hydroxy-pyridazin(3)yl]-thiolmethane-, ethane-, n-propane- and isopropanephosphonic acid esters, the corresponding thiono analogues and, in each case, the compounds substituted by methyl in the pyridazine ring in the 4- or 5-position.

3-Hydroxypyridazine derivatives (III) are known and they can be prepared in accordance with customary processes, for example, if $R_3$ represents alkylsulfonyloxy, by reacting the known 1,6-dihydroxypyridazine with alkylsulfonic acid halide. For further processes for the preparation of the known 3-hydroxypyridazine derivatives (III) see, for example: T. Jojima and Takeshiba, Agr. Biol. Chem. 38, 1169–1176 (1974); T. Nakagome, yakugaku Zasshi, 82, 1005 (1962), J. Druey, K. Meier and K. Eichenberger, Helv. Chim. Acta 37, 121–133 (1954) and Belgian Patent Specification 813,225.

The following may be mentioned as specific examples: 6-chloro-, 6-bromo-, 6-methylsulfonyloxy-, 6-ethylsulfonyloxy-, 6-methoxy-, 6-ethoxy-, 6-n-propoxy-, 6-isopropoxy-, 6-propargyloxy-, 6-N-methyl-carbamoyloxy-, 6-N-ethylcarbamoyloxy-, 6-benzyloxy-, 6-benzoyloxy-, 6-(2-nitro-4-trifluoromethylphenyloxy)-, 6-(2,4-dichlorophenyloxy)-, 6-(2,5-dichlorophenyloxy)-, 6-(2,4,6-trichlorophenyloxy)-, 6-(2-methylthiophenyloxy)-, 6-(2-ethylthiophenyloxy)-, 6-(4-methylthio- and 4-ethylthiophenyloxy)-, 6-(2-nitro- and 4-nitro-phenyloxy)-, 6-(4-cyanophenyloxy)-, 6-(2- and 4-methyl- and -ethyl-phenyloxy)-, 6-(2,4-dimethylphenyloxy)-, 6-(2,4-diethyl-phenyloxy)-, 6-(3-methyl-4-methylthiophenyloxy)-and 6-(3-ethyl-4-methylthiophenyloxy)-3-oxo-pyridazine and the corresponding derivatives which are substituted by methyl or ethyl in the 4- or 5-position in the pyridazine ring.

The acyl halides (V) and the alkyl isocyanates (VI) are known and can be prepared in accordance with generally customary processes described in the literature.

The following may be mentioned specifically as examples of these compounds: methylsulfonyl chloride, ethylsulfonyl chloride and benzoyl chloride, and methyl isocyanate, ethyl isocyanate, n-propyl isocyanate and isopropyl isocyanate.

The process variants (a) to (c) for the preparation of the compounds according to the invention are preferably carried out in the presence of suitable solvents and diluents. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents may be used as acid acceptors in process variants (a) and (b).

Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine. Process variant (c) can optionally be carried out in the presence of a catalytic amount of a tert. organic base, for example diazabicyclooctane or triethylamine.

In all process variants, the reaction temperature can be varied within a substantial range. In general, the reaction is carried out at between 0° and 120° C., preferably at from 10° to 60° C.

The reaction is in general allowed to take place under normal pressure.

To carry out variants (a) and (b), the reactants are preferably employed in equimolar amounts. An excess of one or other component produces no significant advantages. In process variant (c), the alkyl isocyanate component is preferably added in 10 to 15% excess.

In all variants, the reaction is in general carried out in one of the above-mentioned solvents at the stated temperatures. After completion of the reaction, the batch can be worked up as described below. In process variant (a) the reaction mixture is filtered and then poured into an organic solvent, and the organic layer is worked up in the usual manner, while in process variants (b) and (c) the reaction solution is worked up directly, for example by washing, drying and stripping off the solvent, or by directly distilling off the latter.

The new compounds are mostly obtained in the form of oils, which frequently cannot be distilled without decomposition, but are freed from the last volatile constituents by so-called "slight distillation", that is to say by prolonged heating under reduced pressure to moderately elevated temperatures, and are purified in this way. They are characterized by the refractive index. Some of the compounds are obtained in a crystalline form; these are characterized by their melting points.

As already mentioned, the pyridazinyl(thiono)thiol)-phosphonic acid esters according to the invention are distinguished by an excellent insecticidal, acaricidal and nematicidal activity. They are active against plant pests, pests harmful to health and pests of stored products and combine a low phytotoxicity with a good action against both sucking and biting insects and against mites; most of the compounds furthermore exhibit a fungicidal action.

For this reason, the compounds according to the invention can be employed successfully as pesticides in plant protection and also in the hygiene field and the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta Americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the process products are also distinguished by an outstanding residual activity on wood and clay, as well as a good stability to alkali on limed substrates.

The active compounds according to the invention couple a low toxicity to warm-blooded animals with powerful nematicidal properties and can therefore be used to combat nematodes, especially phytopathogenic nematodes. These essentially include leaf nematodes (*Arphelenchoides*), such as the chrysanthemum eelworm (*A. ritzemabosi*), the leaf-bloth eelworm (*A.fragariae*) and the rice eelworm (*A. oryzae*); stem nematodes (*Ditylenchus*), such as the stem eelworm (*D. Dipsaci*); root-knot nematodes (*Meloidogyne*), such as *M. arenaria* and *M. incognita;* cyst-forming nematodes (*Heterodera*), such as the potato cyst eelworm (*H. rostochiensis*) and the beet cyst eelworm (*H. schachtii*); and also free-living root nematodes, for example of the genera *Pratylenchus, Paratylenchus, Rotylenchus, Xiphinema* and *Radopholus.*

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol mono-methyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, nematicides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids, nematodes and fungi, and more particularly methods of combating insects, acarids and nematodes, which comprises applying to at least one of correspondingly (a) such insects, (b) such acarids, (c) such nematodes, (d) such fungi, and (e) the corresponding habitat thereof, i.e. the locus to be protected, e.g. to a growing crop, to an area where a crop is to be grown or to a domestic animal, a correspondingly combative or toxic amount, i.e. an insecticidally, acaricidally, nematocidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

*Drosophila* test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 $cm^3$ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following table:

Table 1
(*Drosophila* test)

| Active compound | | Active compound concentration in % | Degree of destruction in % after 1 day |
|---|---|---|---|
| (known) (A) | | 0.1<br>0.01<br>0.001 | 100<br>50<br>0 |
| (8) | | 0.1<br>0.01<br>0.001 | 100<br>100<br>50 |
| (2) | | 0.1<br>0.01<br>0.001 | 100<br>100<br>98 |
| | (9) | 0.1<br>0.01<br>0.001 | 100<br>100<br>50 |
| | (29) | 0.1<br>0.01<br>0.001 | 100<br>100<br>100 |
| | (43) | 0.1<br>0.01<br>0.001 | 100<br>100<br>90 |
| | (7) | 0.1<br>0.01<br>0.001 | 100<br>100<br>50 |
| | (17) | 0.1<br>0.01<br>0.001 | 100<br>100<br>100 |
| Isomer | (28) | 0.1<br>0.01<br>0.001 | 100<br>100<br>100 |

Table 1-continued

| Active compound | (Drosophila test) | Active compound concentration in % | Degree of destruction in % after 1 day |
|---|---|---|---|
| isoC₃H₇O—⟨phenyl⟩—O—C(=N—N)—CH=C—O—P(=S)(OC₂H₅)(C₂H₅) | (23) | 0.1<br>0.01<br>0.001 | 100<br>100<br>100 |
| CH≡C—CH₂—O—⟨ring⟩—O—P(=S)(OC₂H₅)(C₂H₅), N—N | (33) | 0.1<br>0.01<br>0.001 | 100<br>100<br>40 |
| C₆H₅—O—⟨ring⟩—O—P(=S)(OC₂H₅)(C₂H₅), N—N | (42) | 0.1<br>0.01<br>0.001 | 100<br>100<br>100 |
| NO₂—⟨C₆H₄⟩—O—⟨ring⟩—O—P(=S)(OC₂H₅)(CH₃), N—N | (54) | 0.1<br>0.01<br>0.001 | 100<br>100<br>100 |
| NO₂—⟨C₆H₄⟩—O—⟨ring⟩—O—P(=S)(OC₃H₇-n)(CH₃), N—N | (53) | 0.1<br>0.01<br>0.001 | 100<br>100<br>100 |
| NO₂—⟨C₆H₄⟩—O—⟨ring⟩—O—P(=S)(OC₂H₅)(C₂H₅), N—N | (52) | 0.1<br>0.01<br>0.001 | 100<br>100<br>80 |

EXAMPLE 2

Phaedon larvae test
 Solvent: 3 parts by weight of acetone
 Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dripping wet and were then infested with mustard beetle larvae (Phaedon cochleariae).

After the specified periods of time, the degree of destruction was determined in %: 100% means that all beetle larvae had been killed whereas 0% means that none of the beetle larvae had been killed.

The active compounds, the concentrations of the active compounds, the evaluation times and the results can be seen from the following table:

Table 2

| Active compound | (Phaedon larvae test) | Active compound concentration in % | Degree of destruction in % after 3 days |
|---|---|---|---|
| O=⟨ring⟩—O—P(=S)(CH₃)(OC₂H₅), N—N—H (known) | (D) | 0.01<br>0.001 | 100<br>0 |
| O=⟨ring⟩—O—P(=S)(OC₂H₅)₂, N—N—H (known) | (A) | 0.01<br>0.001 | 100<br>0 |
| (CH₃)₂N—C(=O)—O—⟨ring⟩—O—P(=S)(OC₂H₅)₂, N—N (known) | (C) | 0.01<br>0.001 | 100<br>0 |
| CH₃—SO₂—O—⟨ring⟩—O—P(=S)(OC₃H₇-iso)(CH₃), N—N | (35) | 0.01<br>0.001 | 100<br>100 |

Table 2-continued (Phaedon larvae test)

| Active compound | | Active compound concentration in % | Degree of destruction in % after 3 days |
|---|---|---|---|
| CH₃S–⟨phenyl⟩–O–⟨pyridazine N–N⟩–O–P(=S)(OC₃H₇-iso)(CH₃) | (40) | 0.01<br>0.001 | 100<br>80 |
| CH₃S–⟨phenyl⟩–O–⟨pyridazine N–N⟩–O–P(=S)(OC₂H₅)(C₂H₅) | (41) | 0.01<br>0.001 | 100<br>100 |
| Br–⟨pyridazine N–N⟩–O–P(=S)(OC₃H₇-iso)(CH₃) | (11) | 0.01<br>0.001 | 100<br>95 |
| CH≡C–CH₂–O–⟨pyridazine N=N⟩–O–P(=S)(OC₃H₇-iso)(CH₃) | (32) | 0.01<br>0.001 | 100<br>100 |
| NO₂–⟨phenyl⟩–O–⟨pyridazine N–N⟩–O–P(=S)(OC₂H₅)(CH₃) | (54) | 0.01<br>0.001 | 100<br>100 |
| NC–⟨phenyl⟩–O–⟨pyridazine N–N⟩–O–P(=S)(OC₂H₅)(C₂H₅) | (50) | 0.01<br>0.001 | 100<br>100 |
| NO₂–⟨phenyl⟩–O–⟨pyridazine N–N⟩–O–P(=S)(OC₂H₅)(C₂H₅) | (52) | 0.01<br>0.001 | 100<br>100 |
| (CH₃)(CH₃)–⟨phenyl⟩–O–⟨pyridazine N–N⟩–O–P(=S)(OC₃H₇-iso)(CH₃) | (47) | 0.01<br>0.001 | 100<br>100 |
| ⟨phenyl⟩–O–⟨pyridazine N–N⟩–O–P(=S)(OC₃H₇-iso)(CH₃) | (51) | 0.01<br>0.001 | 100<br>100 |
| NO₂–⟨phenyl⟩–O–⟨pyridazine N–N⟩–O–P(=S)(OC₃H₇-iso)(CH₃) | (53) | 0.01<br>0.001 | 100<br>100 |

EXAMPLE 3

Plutella test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 3

| Active compound | | Active compound concentration in % | Degree of destruction in % after 3 days |
|---|---|---|---|
| *(Plutella test)* | | | |
| O=⟨pyridazinone⟩-O-P(S)(OC$_2$H$_5$)$_2$ (known) | (A) | 0.1<br>0.01<br>0.001 | 100<br>80<br>0 |
| (CH$_3$)$_2$N-C(O)-O-⟨pyridazine⟩-O-P(S)(OC$_2$H$_5$)$_2$ (known) | (C) | 0.1<br>0.01<br>0.001 | 100<br>100<br>0 |
| CH$_3$O-⟨pyridazine⟩-O-P(S)(OC$_3$H$_7$-n)(C$_2$H$_5$) | (20) | 0.1<br>0.01<br>0.001 | 100<br>100<br>100 |
| Cl-⟨pyridazine⟩-O-P(S)(OC$_4$H$_9$-iso)(C$_2$H$_5$) | (14) | 0.1<br>0.01<br>0.001 | 100<br>100<br>100 |
| 2,4-Cl$_2$-C$_6$H$_3$-O-⟨pyridazine⟩-O-P(S)(OC$_3$H$_7$-iso)(CH$_3$) | (38) | 0.1<br>0.01<br>0.001 | 100<br>100<br>100 |
| 2,4-Cl$_2$-C$_6$H$_3$-O-⟨pyridazine⟩-O-P(S)(OC$_2$H$_5$)(C$_2$H$_5$) | (37) | 0.1<br>0.01<br>0.001 | 100<br>100<br>100 |
| 4-F$_3$C-2-NO$_2$-C$_6$H$_3$-O-⟨pyridazine⟩-O-P(S)(OC$_2$H$_5$)(C$_2$H$_5$) | (16) | 0.1<br>0.01<br>0.001 | 100<br>100<br>100 |
| C$_6$H$_5$-CH$_2$-O-⟨pyridazine⟩-O-P(S)(OC$_2$H$_5$)(OC$_2$H$_5$) | (25) | 0.1<br>0.01<br>0.001 | 100<br>100<br>100 |
| 4-NC-C$_6$H$_4$-O-⟨pyridazine⟩-O-P(S)(OC$_3$H$_7$-iso)(CH$_3$) | (51) | 0.1<br>0.01<br>0.001 | 100<br>100<br>95 |
| 4-NC-C$_6$H$_4$-O-⟨pyridazine⟩-O-P(S)(OC$_2$H$_5$)(C$_2$H$_5$) | (50) | 0.1<br>0.01<br>0.001 | 100<br>100<br>100 |
| 4-NO$_2$-C$_6$H$_4$-O-⟨pyridazine⟩-O-P(S)(OC$_2$H$_5$)(C$_2$H$_5$) | (52) | 0.1<br>0.01<br>0.001 | 100<br>100<br>100 |

EXAMPLE 4

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 4
(*Myzus* test)

| Active compound | | Active compound concentration in % | Degree of destruction in % after 1 day |
|---|---|---|---|
| [structure: pyridazinone with S=P(OCH_3)(OC_2H_5)] (known) | (D) | 0.1<br>0.01<br>0.001 | 100<br>90<br>0 |
| [structure with CH_3, Cl, S=P(OC_3H_7-iso)(CH_3)] Isomer mixture | (18) | 0.1<br>0.01<br>0.001 | 100<br>100<br>98 |
| [structure: CH_3—SO_2—O—pyridazine—O—P(S)(OC_3H_7-iso)(CH_3)] | (35) | 0.1<br>0.01<br>0.001 | 100<br>100<br>100 |
| [structure: iso-C_3H_7O—pyridazine—O—P(S)(OC_3H_7-iso)(CH_3)] | (24) | 0.1<br>0.01<br>0.001 | 100<br>100<br>80 |
| [structure: C_6H_5—CH_2—O—pyridazine—O—P(S)(OC_3H_7-iso)(CH_3)] | (26) | 0.1<br>0.01<br>0.001 | 100<br>100<br>65 |
| [structure: CH_3O—pyridazine—O—P(S)(OCH_3)(C_2H_5)] | (22) | 0.1<br>0.01<br>0.001 | 100<br>100<br>98 |
| [structure: C_2H_5O—pyridazine—O—P(S)(OCH_3)(C_2H_5)] | (30) | 0.1<br>0.01<br>0.001 | 100<br>100<br>70 |
| [structure: CH_3—SO_2—O—pyridazine—O—P(S)(OC_2H_5)(C_2H_5)] | (12) | 0.1<br>0.01<br>0.001 | 100<br>100<br>99 |
| [structure with CH_3, Cl, S=P(OC_2H_5)(C_2H_5)] Isomer mixture | (19) | 0.1<br>0.01<br>0.001 | 100<br>100<br>99 |
| [structure: CH_3O—pyridazine—O—P(S)(OC_2H_5)(C_2H_5)] | (15) | 0.1<br>0.01<br>0.001 | 100<br>100<br>95 |
| [structure: C_2H_5O—pyridazine—O—P(S)(OC_2H_5)(C_2H_5)] | (28) | 0.1<br>0.01<br>0.001 | 100<br>100<br>100 |

Table 4-continued (*Myzus* test)

| Active compound | | Active compound concentration in % | Degree of destruction in % after 1 day |
|---|---|---|---|
| iso-$C_3H_7$-O—[pyridazine]—O—P(S)(O$C_2H_5$)($C_2H_5$) | (23) | 0.1<br>0.01<br>0.001 | 100<br>100<br>99 |
| Cl—[pyridazine]—O—P(S)(O$C_2H_5$)($C_2H_5$) | (1) | 0.1<br>0.01<br>0.001 | 100<br>100<br>90 |
| Br—[pyridazine]—O—P(S)(O$C_2H_5$)($C_2H_5$) | (10) | 0.1<br>0.01<br>0.001 | 100<br>100<br>99 |
| $C_6H_5$—$CH_2$—O—[pyridazine]—O—P(S)(O$C_2H_5$)($C_2H_5$) | (25) | 0.1<br>0.01<br>0.001 | 100<br>99<br>99 |
| Cl—[pyridazine]—O—P(S)(O$C_3H_7$-n)($C_2H_5$) | (6) | 0.1<br>0.01<br>0.001 | 100<br>100<br>95 |
| $NO_2$—$C_6H_4$—O—[pyridazine]—O—P(S)(O$C_2H_5$)($C_2H_5$) | (52) | 0.1<br>0.01<br>0.001 | 100<br>100<br>100 |

EXAMPLE 5

Tetranychus test (resistant)
  Solvent: 3 parts by weight of acetone
  Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (Phaseolus vulgaris), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 5

(*Tetranychus* test)

| Active compound | | Active compound concentration in % | Degree of destruction in % after 2 days |
|---|---|---|---|
| O=[pyridazine-NH]—O—P(S)(O$C_2H_5$)$_2$ (known) | | 0.1<br>0.01 | 20<br>0 |
| O=[pyridazine-NH]—O—P(S)($CH_3$)(O$C_2H_5$) (known) | (A) | 0.1<br>0.01 | 95<br>0 |
| O=[pyridazine-NH]—O—P(S)($C_2H_5$)(O$C_2H_5$) | (D) | 0.1<br>0.01 | 95<br>0 |

Table 5-continued
(*Tetranychus* test)

| Active compound | | Active compound concentration in % | Degree of destruction in % after 2 days |
|---|---|---|---|
| (known) $CH_3O-\underset{N=N}{\underset{|}{\bigcirc}}-O-\overset{S}{\underset{C_2H_5}{\overset{\|}{P}}}-OCH_3$ | (E) (22) | 0.1 0.01 | 100 80 |
| $Cl-\underset{N=N}{\underset{|}{\bigcirc}}\overset{CH_3}{\underset{}{}}-O-\overset{S}{\underset{C_2H_5}{\overset{\|}{P}}}-OCH_3$ Isomer mixture | (17) | 0.1 0.01 | 100 70 |
| $CH_3-SO_2-O-\underset{N=N}{\underset{|}{\bigcirc}}-O-\overset{S}{\underset{C_2H_5}{\overset{\|}{P}}}-OCH_3$ | (34) | 0.1 0.01 | 100 90 |
| $CH_3O-\underset{N=N}{\underset{|}{\bigcirc}}-O-\overset{S}{\underset{C_2H_5}{\overset{\|}{P}}}-OC_2H_5$ | (15) | 0.1 0.01 | 100 70 |
| $Cl-\underset{N=N}{\underset{|}{\bigcirc}}\overset{CH_3}{\underset{}{}}-O-\overset{S}{\underset{C_2H_5}{\overset{\|}{P}}}-OC_2H_5$ Isomer mixture | (19) | 0.1 0.01 | 100 95 |
| $CH_3-SO_2-O-\underset{N=N}{\underset{|}{\bigcirc}}-O-\overset{S}{\underset{C_2H_5}{\overset{\|}{P}}}-OC_2H_5$ | (12) | 0.1 0.01 | 100 98 |
| $CH\equiv C-CH_2-O-\underset{N=N}{\underset{|}{\bigcirc}}-O-\overset{S}{\underset{C_2H_5}{\overset{\|}{P}}}-OC_2H_5$ | (33) | 0.1 0.01 | 100 60 |
| $isoC_3H_7O-\underset{N=N}{\underset{|}{\bigcirc}}-O-\overset{S}{\underset{C_2H_5}{\overset{\|}{P}}}-OC_2H_5$ | (23) | 0.1 0.01 | 100 90 |
| $Cl-\underset{N=N}{\underset{|}{\bigcirc}}-O-\overset{S}{\underset{C_2H_5}{\overset{\|}{P}}}-OC_2H_5$ | (1) | 0.1 0.01 | 100 98 |
| $Br-\underset{N=N}{\underset{|}{\bigcirc}}-O-\overset{S}{\underset{C_2H_5}{\overset{\|}{P}}}-OC_2H_5$ | (10) | 0.1 0.01 | 100 70 |
| $CH_3O-\underset{N=N}{\underset{|}{\bigcirc}}-O-\overset{S}{\underset{C_2H_5}{\overset{\|}{P}}}-OC_3H_7\text{-}n$ | (20) | 0.1 0.01 | 100 60 |
| $Cl-\underset{N=N}{\underset{|}{\bigcirc}}-O-\overset{S}{\underset{C_2H_5}{\overset{\|}{P}}}-OC_3H_7\text{-}n$ | (6) | 0.1 0.01 | 100 95 |

Table 5-continued
(*Tetranychus* test)

| Active compound | | Active compound concentration in % | Degree of destruction in % after 2 days |
|---|---|---|---|
| [structure: 6-chloro-4,4-dimethyl pyridazinone with O-P(=S)(OC₃H₇-iso)(C₂H₅)] Isomer mixture | (21) | 0.1<br>0.01 | 100<br>70 |
| [structure: 6-chloropyridazine-3-yl O-P(=S)(OC₄H₉-iso)(C₂H₅)] | (14) | 0.1<br>0.01 | 100<br>99 |
| [structure: 6-methoxypyridazine-3-yl O-P(=S)(CH₃)(OC₃H₇-iso)] | (2) | 0.1<br>0.01 | 100<br>99 |
| [structure: 6-chloro-4-methyl pyridazinone with O-P(=S)(OC₃H₇-iso)(CH₃)] Isomer mixture | (18) | 0.1<br>0.01 | 100<br>100 |
| [structure: CH₃-SO₂-O-pyridazinyl-O-P(=S)(OC₃H₇-iso)(CH₃)] | (35) | 0.1<br>0.01 | 100<br>100 |
| [structure: CH₃-NH-CO-O-pyridazinyl-O-P(=S)(OC₃H₇-iso)(CH₃)] | (3) | 0.1<br>0.01 | 100<br>80 |
| [structure: CH₃-S-C₆H₄-O-pyridazinyl-O-P(=S)(OC₃H₇-iso)(CH₃)] | (40) | 0.1<br>0.01 | 98<br>80 |
| [structure: C₂H₅O-pyridazinyl-O-P(=S)(OC₃H₇-iso)(CH₃)] | (29) | 0.1<br>0.01 | 100<br>60 |
| [structure: CH≡C-CH₂-O-pyridazinyl-O-P(=S)(OC₃H₇-iso)(CH₃)] | (32) | 0.1<br>0.01 | 100<br>98 |
| [structure: iso-C₃H₇O-pyridazinyl-O-P(=S)(OC₃H₇-iso)(CH₃)] | (24) | 0.1<br>0.01 | 100<br>100 |
| [structure: Cl-pyridazinyl-O-P(=S)(OC₃H₇-iso)(CH₃)] | (9) | 0.1<br>0.01 | 100<br>98 |
| [structure: Br-pyridazinyl-O-P(=S)(OC₃H₇-iso)(CH₃)] | (11) | 0.1<br>0.01 | 100<br>100 |

EXAMPLE 6

Critical concentration test/soil insects
Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is hereinafter quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Table 6

Critical concentration test/soil insects (*Phorbia antiqua* grubs in the soil)

| Active compound | | Degree of destruction in % at an active compound concentration of 20 ppm |
|---|---|---|
| 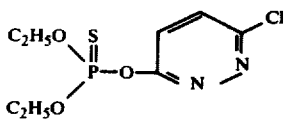 (known) | (B) | 0 |
| 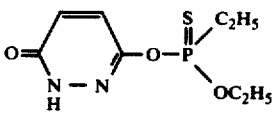 (known) | (E) | 0 |
| 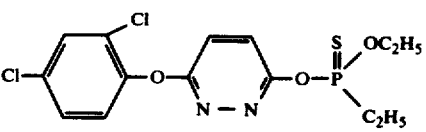 | (37) | 100 |
| 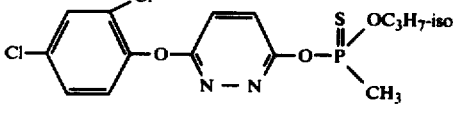 | (38) | 100 |
| 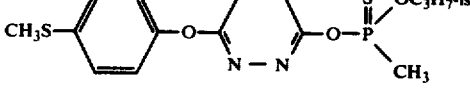 | (40) | 100 |
| 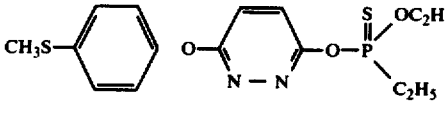 | (41) | 100 |
| 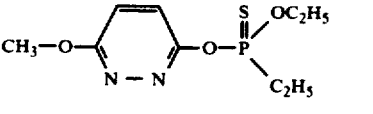 | (15) | 100 |
| 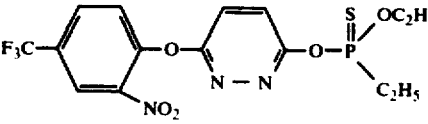 | (16) | 100 |

Table 6-continued

Critical concentration test/soil insects
*(Phorbia antiqua grubs in the soil)*

| Active compound | | Degree of destruction in % at an active compound concentration of 20 ppm |
|---|---|---|
| [structure: 6-chloro-4-methyl-pyridazin-3-yl O-isopropyl methyl phosphonothioate] Isomer mixture | (18) | 100 |
| [structure: 6-chloro-4-methyl-pyridazin-3-yl O-ethyl ethyl phosphonothioate] Isomer mixture | (19) | 100 |
| [structure: 6-methoxy-pyridazin-3-yl O-isopropyl methyl phosphonothioate] | (2) | 100 |
| [structure: 6-methoxy-pyridazin-3-yl O-n-propyl ethyl phosphonothioate] | (20) | 100 |
| [structure: 6-chloro-4-methyl-pyridazin-3-yl O-isopropyl ethyl phosphonothioate] Isomer mixture | (21) | 100 |
| [structure: 6-methoxy-pyridazin-3-yl O-methyl ethyl phosphonothioate] | (22) | 100 |
| [structure: 6-isopropoxy-pyridazin-3-yl O-ethyl ethyl phosphonothioate] | (23) | 100 |
| [structure: 6-isopropoxy-pyridazin-3-yl O-isopropyl methyl phosphonothioate] | (24) | 100 |
| [structure: 6-benzyloxy-pyridazin-3-yl O-ethyl ethyl phosphonothioate] | (25) | 100 |
| [structure: 6-benzyloxy-pyridazin-3-yl O-isopropyl methyl phosphonothioate] | (26) | 100 |
| [structure: 6-chloro-pyridazin-3-yl O-n-propyl ethyl phosphonothioate] | (6) | 100 |

Table 6-continued

| Critical concentration test/soil insects (*Phorbia antiqua* grubs in the soil) | | Degree of destruction in % at an active compound concentration of 20 ppm |
|---|---|---|
| Active compound | | |
| CH$_3$—SO$_2$—O—[pyridazine]—O—P(=S)(OC$_2$H$_5$)(C$_2$H$_5$) | (12) | 100 |
| Cl—[pyridazine]—O—P(=S)(OC$_4$H$_9$-iso)(C$_2$H$_5$) | (14) | 100 |
| C$_2$H$_5$O—[pyridazine]—O—P(=S)(OC$_2$H$_5$)(C$_2$H$_5$) | (28) | 100 |
| C$_2$H$_5$O—[pyridazine]—O—P(=S)(OCH$_3$)(C$_2$H$_5$) | (30) | 100 |

EXAMPLE 7

Critical concentration test/soil insects
   Test insect: *Tenebrio molitor* larvae in the soil
   Solvent: 3 parts by weight of acetone
   Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Table 7

| Critical concentration test/soil insects (*Tenebrio molitor* larvae in the soil) | | Degree of destruction in % at an active compound concentration of 5 ppm |
|---|---|---|
| Active compound | | |
| O=[pyridazine-NH]—O—P(=S)(C$_2$H$_5$)(OC$_2$H$_5$) (known) | (E) | 0 |
| CH$_3$O—[pyridazine]—O—P(=S)(OC$_3$H$_7$-n)(C$_2$H$_5$) | (20) | 100 |
| Cl—[pyridazine-CH$_3$]—O—P(=S)(OC$_3$H$_7$-iso)(CH$_3$)  Isomer mixture | (18) | 100 |

Table 7-continued

| Active compound | | Critical concentration test/soil insects (*Tenebrio molitor* larvae in the soil) Degree of destruction in % at an active compound concentration of 5 ppm |
|---|---|---|
| 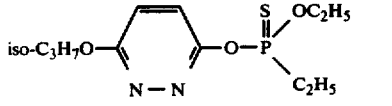 iso-C₃H₇O—⟨N—N⟩—O—P(=S)(OC₂H₅)(C₂H₅) | (23) | 100 |
| 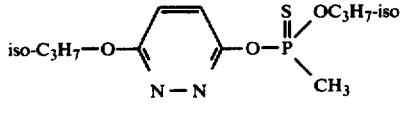 iso-C₃H₇—O—⟨N—N⟩—O—P(=S)(OC₃H₇-iso)(CH₃) | (24) | 100 |
| 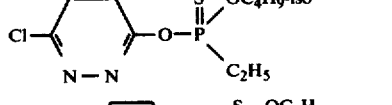 Cl—⟨N—N⟩—O—P(=S)(OC₄H₉-iso)(C₂H₅) | (4) | 100 |
| 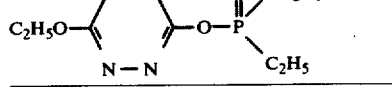 C₂H₅O—⟨N—N⟩—O—P(=S)(OC₂H₅)(C₂H₅) | (20) | 100 |

EXAMPLE 8

Critical concentration test/nematodes
  Test nematode: *Meloidogyne incognita*
  Solvent: 3 parts by weight of acetone
  Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm, was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 8

| Active compound | | Critical concentration test/nematodes (*Meloidogyne incognita*) Degree of destruction in % at an active compound concentration of 20 ppm |
|---|---|---|
| 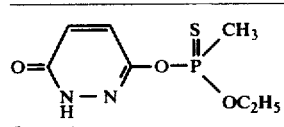 O=⟨NH—N⟩—O—P(=S)(CH₃)(OC₂H₅) (known) | (D) | 0 |
| 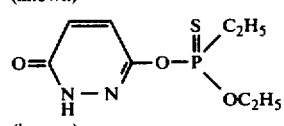 O=⟨NH—N⟩—O—P(=S)(C₂H₅)(OC₂H₅) (known) | (E) | 0 |
| 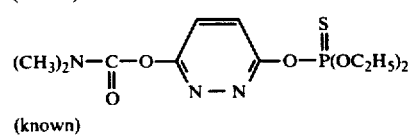 (CH₃)₂N—C(=O)—O—⟨N—N⟩—O—P(=S)(OC₂H₅)₂ (known) | (C) | 0 |
| 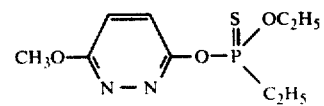 CH₃O—⟨N—N⟩—O—P(=S)(OC₂H₅)(C₂H₅) | (15) | 100 |

Table 8-continued

Critical concentration test/nematodes (*Meloidogyne incognita*)

| Active compound | | Degree of destruction in % at an active compound concentration of 20 ppm |
|---|---|---|
| [Structure: Cl–C(=N–N=)–C(CH₃)=CH–CH=C(O–P(=S)(OC₂H₅)(C₂H₅))] Isomer mixture | (19) | 100 |
| [Structure: CH₃O–C(=N–N=)–CH=CH–CH=C(O–P(=S)(OC₃H₇-n)(C₂H₅))] | (20) | 100 |
| [Structure: Cl–C(=)–C(CH₃)=CH–CH=CH–C(O–P(=S)(OC₃H₇-iso)(C₂H₅))] Isomer mixture | (21) | 100 |
| [Structure: Cl–C(=N–N=)–CH=CH–CH=C(O–P(=S)(OC₄H₉-iso)(C₂H₅))] | (14) | 100 |
| [Structure: C₂H₅O–C(=N–N=)–CH=CH–CH=C(O–P(=S)(OC₂H₅)(C₂H₅))] | (28) | 100 |
| [Structure: iso-C₃H₇O–C(=N–N=)–CH=CH–CH=C(O–P(=S)(OC₂H₅)(C₂H₅))] | (23) | 100 |

EXAMPLE 9

LT$_{100}$ test for Diptera

Test insects: *Aëdes aegypti*

Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 9

(LT$_{100}$ test for *Diptera/Aedes aegypti*)

| Active compound | Active compound concentration of the solution in % | LT$_{100}$ in minutes (') or hours (hrs) |
|---|---|---|
| [Structure: O=C–NH–N=CH–CH=C(O–P(=S)(C₂H₅)(OC₂H₅))] (known) (E) | 0.2 | 180' |
| [Structure: (CH₃)₂N–C(=O)–O–C(=N–N=)–CH=CH–CH=C(O–P(=S)(OC₂H₅)₂)] (known) (C) | 0.2<br>0.02 | 60'<br>3 hrs = 60% |

Table 9-continued (LT$_{100}$ test for *Diptera/Aedes aegypti*)

| Active compound | Active compound concentration of the solution in % | LT$_{100}$ in minutes (') or hours (hrs) |
|---|---|---|
| [structure: CH$_3$O-pyridazine-O-P(=S)(OC$_2$H$_5$)(C$_2$H$_5$)] | (15) 0.2<br>0.02<br>0.002 | 60'<br>120'<br>3 hrs = 80% |
| [structure: CH$_3$O-pyridazine-O-P(=S)(OCH$_3$)(C$_2$H$_5$)] | (22) 0.2<br>0.02<br>0.002 | 60'<br>60'<br>180' |
| [structure: CH$_3$O-pyridazine-O-P(=S)(OC$_3$H$_7$-n)(C$_2$H$_5$)] | (20) 0.2<br>0.02<br>0.002 | 60'<br>60'<br>180' |
| [structure: tetrahydropyridazine with OCH$_3$, N-CH$_3$, O-P(=S)(OC$_3$H$_7$-iso)(CH$_3$)] | (2) 0.2<br>0.02<br>0.002 | 60'<br>60'<br>120' |
| [structure: C$_2$H$_5$O-pyridazine-O-P(=S)(OC$_2$H$_5$)(C$_2$H$_5$)] | (28) 0.2<br>0.02<br>0.002 | 60'<br>60'<br>180' |
| [structure: C$_2$H$_5$O-pyridazine-O-P(=S)(OCH$_3$)(C$_2$H$_5$)] | (30) 0.2<br>0.02 | 60'<br>120' |
| [structure: C$_2$H$_5$O-pyridazine-O-P(=S)(OC$_3$H$_7$-iso)(CH$_3$)] | (29) 0.2<br>0.02 | 60'<br>60' |
| [structure: tetrahydropyridazine with O-C$_3$H$_7$-n, N-C$_2$H$_5$, O-P(=S)(OC$_2$H$_5$)(C$_2$H$_5$)] | 0.2<br>0.02<br>0.002 | 60'<br>60'<br>180' |
| [structure: tetrahydropyridazine with O-C$_3$H$_7$-n, N-CH$_3$, O-P(=S)(OC$_3$H$_7$-n)(CH$_3$)] | 0.2<br>0.02<br>0.002 | 60'<br>120'<br>3 hrs = 70% |

Table 9-continued
(LT₁₀₀ test for *Diptera/Aedes aegypti*)

| Active compound | | Active compound concentration of the solution in % | $LT_{100}$ in minutes (') or hours (hrs) |
|---|---|---|---|
| HC≡C—CH₂—O—[pyridazine]—O—P(=S)(OC₂H₅)(C₂H₅) | (33) | 0.2<br>0.02 | 60'<br>120' |
| HC≡C—CH₂—O—[pyridazine]—O—P(=S)(OC₃H₇-iso)(CH₃) | (32) | 0.2<br>0.02 | 60'<br>120' |
| Cl—[pyridazine]—O—P(=S)(OCH₃)(C₂H₅) | (7) | 0.2<br>0.02<br>0.002 | 60'<br>60'<br>180' |
| Cl—[pyridazine]—O—P(=S)(OC₂H₅)(C₂H₅) | (1) | 0.2<br>0.02<br>0.002 | 60'<br>60'<br>120' |
| Cl—[pyridazine]—O—P(=S)(OC₃H₇-n)(C₂H₅) | (6) | 0.2<br>0.02 | 60'<br>120' |
| Cl—[pyridazine]—O—P(=S)(OC₂H₅)(CH₃) | (8) | 0.2<br>0.02<br>0.002 | 60'<br>60'<br>180' |
| Cl—[pyridazine]—O—P(=S)(OC₃H₇-iso)(CH₃) | (9) | 0.2<br>0.02<br>0.002 | 60'<br>60'<br>180' |
| Cl—[pyridazine]—O—P(=S)(OC₄H₉-iso)(C₂H₅) | (14) | 0.2<br>0.02 | 60'<br>120' |
| Br—[pyridazine]—O—P(=S)(OC₂H₅)(C₂H₅) | (10) | 0.2<br>0.02 | 60'<br>120' |
| CH₃—SO₂—O—[pyridazine]—O—P(=S)(CH₃)(OC₂H₅) | (4) | 0.2<br>0.02 | 60'<br>120' |
| [cyclic phosphorodiazine structure with C₂H₅, OCH₃, O—SO₂CH₃] | (34) | 0.2<br>0.02 | 60'<br>180' |
| Br—[pyridazine]—O—P(=S)(OC₃H₇-iso)(CH₃) | (11) | 0.2<br>0.02<br>0.002 | 60'<br>60'<br>180' |

Table 9-continued (LT$_{100}$ test for *Diptera/Aedes aegypti*)

| Active compound | | Active compound concentration of the solution in % | LT$_{100}$ in minutes (') or hours (hrs) |
|---|---|---|---|
| [structure: CH$_3$, Cl, N—N pyridazine with O—P(=S)(OCH$_3$)(C$_2$H$_5$)] Isomer mixture | (17) | 0.2<br>0.02<br>0.002 | 60'<br>60'<br>180' |
| [structure: CH$_3$, Cl, N—N pyridazine with O—P(=S)(OC$_2$H$_5$)(C$_2$H$_5$)] Isomer mixture | (19) | 0.2<br>0.02 | 60'<br>120' |
| [structure: CH$_3$, Cl, N—N pyridazine with O—P(=S)(OC$_3$H$_7$-iso)(CH$_3$)] Isomer mixture | (18) | 0.2<br>0.02<br>0.002 | 60'<br>60'<br>3 hrs = 90% |
| [structure: CH$_3$, Cl, N—N pyridazine with O—P(=S)(OC$_3$H$_7$-n)(C$_2$H$_5$)] Isomer mixture | (21) | 0.2<br>0.02 | 60'<br>120' |
| [structure: phenoxy, N—N pyridazine with O—P(=S)(OC$_2$H$_5$)(C$_2$H$_5$)] | (42) | 0.2<br>0.02 | 60'<br>120' |
| [structure: phenoxy, N—N pyridazine with O—P(=S)(OC$_3$H$_7$-iso)(CH$_3$)] | (43) | 0.2<br>0.02<br>0.002 | 60'<br>120'<br>180' |

EXAMPLE 10

LD$_{100}$ test

Test insects: *Sitophilus granarius*

Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denotes that all of the test insects had been killed; 0% denotes that no test insects had been killed.

The active compounds, the concentrations of the active compounds, the test insects and the results can be seen from the following table:

Table 10
*(LD$_{100}$ test/Sitophilus granarius)*
| Active compound | | Active compound concentration of the solution in % | Degree of destruction in % |
|---|---|---|---|
| 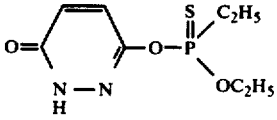 (known) | (E) | 0.2<br>0.02 | 100<br>0 |
| 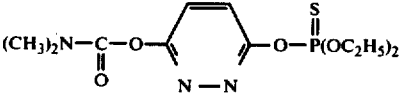 (known) | (C) | 0.2<br>0.02 | 100<br>0 |
| 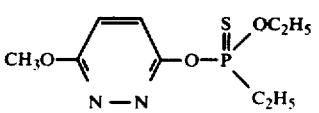 | (15) | 0.2<br>0.02<br>0.002 | 100<br>100<br>30 |
| 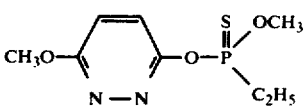 | (22) | 0.2<br>0.02 | 100<br>100 |
| 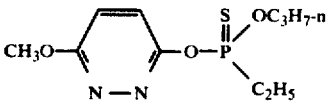 | (20) | 0.2<br>0.02<br>0.002 | 100<br>100<br>50 |
| 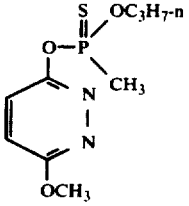 | (63) | 0.2<br>0.02<br>0.002 | 100<br>100<br>100 |
| 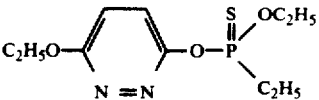 | (28) | 0.2<br>0.02 | 100<br>100 |
| 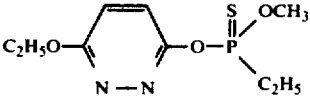 | (30) | 0.2<br>0.02 | 100<br>100 |
| 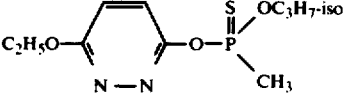 | (29) | 0.2<br>0.02 | 100<br>100 |
| 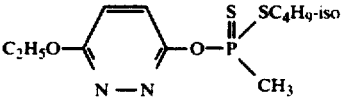 | (27) | 0.2<br>0.02 | 100<br>100 |
| 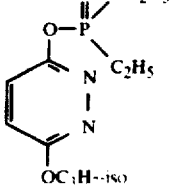 | (23) | 0.2<br>0.02 | 100<br>100 |

Table 10-continued (LD$_{100}$ test/*Sitophilus granarius*)

| Active compound | | Active compound concentration of the solution in % | Degree of destruction in % |
|---|---|---|---|
| [structure: pyridazine with S=P(OC$_3$H$_7$-iso)(CH$_3$), OC$_3$H$_7$-iso] | (24) | 0.2<br>0.02 | 100<br>100 |
| HC≡C—CH$_2$—O—[pyridazine]—O—P(S)(OC$_2$H$_5$)(C$_2$H$_5$) | (33) | 0.2<br>0.02 | 100<br>100 |
| Cl—[pyridazine]—O—P(S)(OCH$_3$)(C$_2$H$_5$) | (7) | 0.2<br>0.02<br>0.002 | 100<br>100<br>100 |
| Cl—[pyridazine]—O—P(S)(OC$_2$H$_5$)(C$_2$H$_5$) | (1) | 0.2<br>0.02<br>0.002 | 100<br>100<br>100 |
| Cl—[pyridazine]—O—P(S)(OC$_3$H$_7$-n)(C$_2$H$_5$) | (6) | 0.2<br>0.02 | 100<br>100 |
| Cl—[pyridazine]—O—P(S)(OC$_2$H$_5$)(CH$_3$) | (8) | 0.2<br>0.02 | 100<br>100 |
| Cl—[pyridazine]—O—P(S)(OC$_3$H$_7$iso)(CH$_3$) | (9) | 0.2<br>0.02<br>0.002 | 100<br>100<br>50 |
| Cl—[pyridazine]—O—P(S)(OC$_4$H$_9$-iso)(C$_2$H$_5$) | (14) | 0.2<br>0.02 | 100<br>100 |
| Br—[pyridazine]—O—P(S)(OC$_2$H$_5$)(C$_2$H$_5$) | (10) | 0.2<br>0.02<br>0.002 | 100<br>100<br>100 |
| Br—[pyridazine]—O—P(S)(OC$_3$H$_7$-iso)(CH$_3$) | (11) | 0.2<br>0.02 | 100<br>100 |
| Cl—[pyridazine with CH$_3$]—O—P(S)(OCH$_3$)(C$_2$H$_5$)<br>Isomer mixture | (17) | 0.2<br>0.02<br>0.002 | 100<br>100<br>60 |
| CH$_3$—[pyridazine with Cl]—O—P(S)(OC$_2$H$_5$)(C$_2$H$_5$)<br>Isomer mixture | (19) | 0.2<br>0.02<br>0.002 | 100<br>100<br>90 |

Table 10-continued (LD₁₀₀ test/*Sitophilus granarius*)

| Active compound | | Active compound concentration of the solution in % | Degree of destruction in % |
|---|---|---|---|
| ![structure with S, OC₃H₇-iso, O-P, N-CH₃, N, Cl, CH₃]<br>Isomer mixture | (18) | 0.2<br>0.02 | 100<br>100 |
| ![structure with S, OC₃H₇-iso, O-P, N-C₂H₅, N, Cl, CH₃]<br>Isomer mixture | (21) | 0.2<br>0.02 | 100<br>100 |
| CH₃—SO₂—O—[ring]—O—P(S)(OC₂H₅)(C₂H₅), N—N | (12) | 0.2<br>0.02 | 100<br>100 |
| [phenyl]—O—[ring]—O—P(S)(OC₂H₅)(C₂H₅), N—N | (42) | 0.2<br>0.02 | 100<br>100 |
| Cl,Cl-[phenyl]—O—[ring]—O—P(S)(OC₂H₅)(C₂H₅), N—N | (37) | 0.2<br>0.02 | 100<br>100 |
| Cl,Cl-[phenyl]—O—[ring]—O—P(S)(OC₃H₇-iso)(CH₃), N—N | (38) | 0.2<br>0.02 | 100<br>100 |
| [phenyl]—CH₂—O—[ring]—O—P(S)(OC₂H₅)(C₂H₅), N—N | (25) | 0.2<br>0.02 | 100<br>100 |

The process of this invention is illustrated by the following preparative Examples.

EXAMPLE 11

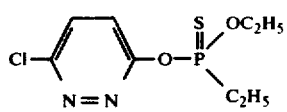
(1)

26.1 g (0.15 mole) of O-ethyl-thionoethanephosphonic acid ester chloride were added dropwise to a mixture of 19.5 g (0.15 mole) of 3-chloro-1,6-dihydro-6-oxo-pyridazine and 21.4 g (0.155 mole) of potassium carbonate in 150 ml of acetonitrile. The mixture was warmed to 40° C. for three hours and was then filtered, and the filtrate was poured into 200 ml of toluene. The toluene solution was washed with saturated sodium carbonate solution and water, dried over sodium sulfate and then concentrated. This gave 34 g (85% of theory) of O-ethyl-O-[6-chloro-pyridazin(3)yl]ethanethionophosphonic acid ester in the form of colorless crystals of melting point 58° C.

EXAMPLE 12

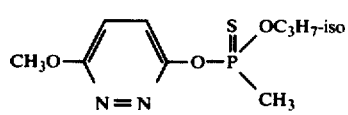
(2)

A mixture of 16.4 g (0.1 mole) of the potassium derivative of 6-methoxy-3-hydroxy-pyridazine, 17.3 g (0.1 mole) of O-isopropyl-thionomethanephosphonic acid ester chloride and 200 ml of acetonitrile was stirred for 3 hours at 50° C. After adding 300 ml of toluene, the reaction mixture was washed twice with 200 ml of water at a time and was dried over sulfate and the solvent was distilled off in vacuo. 19.8 g (76% of theory) of O-isopropyl-O-[6-methoxy-pyridazin(3)yl]-thionomethanephosphonic acid ester were thus obtained in the form of a colorless powder of melting point 61° C.

EXAMPLE 13

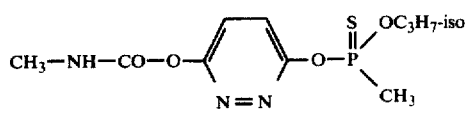

6.3 g (0.11 mole) of methyl isocyanate were added dropwise at 20°-30° C. to a solution of 24.6 g (0.1 mole) of O-isopropyl-O-[6-hydroxy-pyridazin(3)yl]-thionomethanephosphonic acid ester and 0.2 g of diazabicyclooctane in 200 ml of methylene chloride. The mixture was stirred for a further 18 hours at room temperature and then filtered. After evaporating off the solvent, 28 g (92% of theory) of O-isopropyl-O-[6-N-methylcarbamoyloxy-pyridazin(3)yl]-thionomethanephosphonic acid ester remained in the form of colorless crystals of melting point 73° C.

EXAMPLE 14

(a) 1,6-Dihydro-3-methylsulfonyloxy-6-oxopyridazine required as a starting material was prepared as follows:

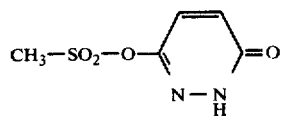

102.9 g (0.9 mole) of methanesulfonic acid chloride were added dropwise at 0° C. to a solution of 100.8 g (0.9 mole) of 1,6-dihydroxypyridazine and 50.4 g (0.9 mole) of potassium hydroxide in 500 ml of water. The mixture was allowed to react for a further hour at 20° C. and was then cooled to −10° C., and the precipitate formed was filtered off. After recrystallization from acetonitrile, 87 g (51% of theory) of 1,6-dihydro-3-methylsulfonyloxy-6-oxopyridazine were obtained in the form of colorless crystals of melting point 148° C.

(b)

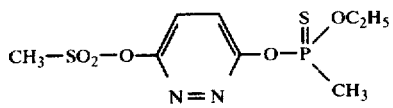

9.5 g (50 mmoles) of O-[6-hydroxy-pyridazin(3)yl]-methanesulphonic acid ester, 8.5 g (55 mmoles) of ground potassium carbonate and 100 ml of acetonitrile were heated to 50° C. while stirring and immediately afterwards were cooled to 30° C., and 7.9 g (50 mmoles) of O-ethyl-methanethiono-phosphonic acid ester chloride were added. The mixture was stirred for a further 30 minutes at room temperature and then for 1 hour at 50° C., and was filtered; the filtrate was evaporated in vacuo. The residue was shaken with 100 ml of toluene and the organic phase was decanted off the sediment, washed with 25 ml of water, dried over magnesium sulfate and worked up in the usual manner. The solid which remained was washed with 25 ml of ether. 9 g (60% of theory) of O-ethyl-O-[6-methylsulfonyloxy-pyridazin(3)yl]-thionomethanephosphonic acid ester were obtained in the form of a colorless powder of melting point 110°-120° C.

EXAMPLE 15

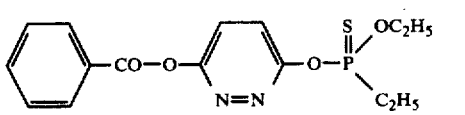

14.0 g (0.1 mole) of benzoyl chloride were added dropwise at 24.8 g (0.1 mole) of O-ethyl-O-[6-hydroxy-pyridazin(3)yl]-thionoethanephosphonic acid ester, 200 ml of methylene chloride and 10.1 g (0.1 mole) of triethylamine at between 20° and 30° C., while stirring. The mixture was then stirred for a further 2 hours at room temperature, the reaction solution was extracted by shaking twice with 100 ml of water at a time and the organic phase was dried over magnesium sulfate and worked up in the usual manner. 27.5 g (78% of theory) of O-ethyl-O-[6-benzoyloxy-pyridazin(3)yl]-thionoethanephosphonic acid ester remained in the form of a light yellow oil of refractive index $n_D^{21}$: 1.5610.

The following compounds of the general formula

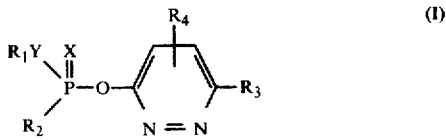

were prepared analogously to one of Examples 11–15. Compounds 17, 18, 19 and 21 are, in each case, isomer mixtures.

| Compound No. | X | Y | $R_1$ | $R_2$ | $R_3$ | $R_4$ | Yield (% of theory) | Physical data (Melting point ° C) (refractive index) |
|---|---|---|---|---|---|---|---|---|
| 6 | S | O | $-C_3H_7-n$ | $-C_2H_5$ | Cl | H | 84 | 105 |
| 7 | S | O | $-CH_3$ | $-C_2H_5$ | Cl | H | 57 | 75 |
| 8 | S | O | $-C_2H_5$ | $-CH_3$ | Cl | H | 57 | 73 |
| 9 | S | O | $-C_3H_7-iso$ | $-CH_3$ | Cl | H | 67 | 77 |
| 10 | S | O | $-C_2H_5$ | $-C_2H_5$ | Br | H | 61 | 63 |
| 11 | S | O | $-C_3H_7-iso$ | $-CH_3$ | Br | H | 62 | 86 |
| 12 | S | O | $-C_2H_5$ | $-C_2H_5$ | $CH_3-SO_2-O-$ | H | 51 | partially crystalline |
| 13 | S | S | $-CH-CH_2-CH_3$<br>\|<br>$CH_3$ | $-CH_3$ | Cl | H | 49 | $n_D^{18}$: 1.5820 |
| 14 | S | O | $-C_4H_9-iso$ | $-C_2H_5$ | Cl | H | 74 | $n_D^{18}$: 1.5267 |
| 15 | S | O | $-C_2H_5$ | $-C_2H_5$ | $CH_3O-$ | H | 69 | $n_D^{20}$: 1.5194 |
| 16 | S | O | $-C_2H_5$ | $-C_2H_5$ | $CF_3-\bigcirc-O-$<br>$NO_2$ | H | 78 | 78 |
| 17 | S | O | $-CH_3$ | $-C_2H_5$ | Cl | $CH_3$ | 47 | $n_D^{20}$: 1.5423 |

-continued

| Compound No. | X | Y | $R_1$ | $R_2$ | $R_3$ | $R_4$ | Yield (% of theory) | Physical data (Melting point °C) (refractive index) |
|---|---|---|---|---|---|---|---|---|
| 18 | S | O | $-C_3H_7$-iso | $-CH_3$ | Cl | $CH_3$ | 30 | $n_D^{20}$: 1.5304 |
| 19 | S | O | $-C_2H_5$ | $-C_2H_5$ | Cl | $CH_3$ | 30 | $n_D^{22}$: 1.5391 |
| 20 | S | O | $-C_3H_7$-n | $-C_2H_5$ | $CH_3O-$ | H | 54 | partially crystalline |
| 21 | S | O | $-C_3H_7$-iso | $-C_2H_5$ | Cl | $CH_3$ | 45 | partially crystalline |
| 22 | S | O | $-CH_3$ | $-C_2H_5$ | $CH_3O-$ | H | 67 | 37 |
| 23 | S | O | $-C_2H_5$ | $-C_2H_5$ | iso-$C_3H_7O-$ | H | 71 | $n_D^{21}$: 1.5143 |
| 24 | S | O | $-C_3H_7$-iso | $-CH_3$ | iso-$C_3H_7O-$ | H | 57 | $n_D^{19}$: 1.5138 |
| 25 | S | O | $-C_2H_5$ | $-C_2H_5$ | Ph-$CH_2-O-$ | H | | |
| 26 | S | O | $-C_3H_7$-iso | $-CH_3$ | Ph-$CH_2-O-$ | H | 52 | 63 |
| 27 | S | S | $-C_4H_9$-sec. | $-CH_3$ | $C_2H_5O-$ | H | 71 | $n_D^{22}$: 1.5440 |
| 28 | S | O | $-C_2H_5$ | $-C_2H_5$ | $C_2H_5O-$ | H | 86 | $n_D^{22}$: 1.5010 |
| 29 | S | O | $-C_3H_7$-iso | $-CH_3$ | $C_2H_5O-$ | H | 82 | $n_D^{22}$: 1.4940 |
| 30 | S | O | $-CH_3$ | $-C_2H_5$ | $C_2H_5O-$ | H | 90 | $n_D^{22}$: 1.5090 |
| 31 | S | O | $-C_2H_5$ | $-CH_3$ | $C_2H_5O-$ | H | 68 | $n_D^{22}$: 1.5210 |
| 32 | S | O | $-C_3H_7$-iso | $-CH_3$ | $CH\equiv C-CH_2O-$ | H | 69 | $n_D^{22}$: 1.5110 |
| 33 | S | O | $-C_2H_5$ | $C_2H_5$ | $CH\equiv C-CH_2O-$ | H | 68 | $n_D^{22}$: 1.5120 |
| 34 | S | O | $-CH_3$ | $-C_2H_5$ | $CH_3-SO_2-O-$ | H | 80 | $n_D^{22}$: 1.5390 |
| 35 | S | O | $-C_3H_7$-iso | $-CH_3$ | $CH_3-SO_2-O-$ | H | 75 | $n_D^{22}$: 1.5230 |
| 36 | S | S | $-C_4H_9$-sec. | $-CH_3$ | $CH_3-SO_2-O-$ | H | 84 | $n_D^{22}$: 1.5620 |
| 37 | S | O | $-C_2H_5$ | $-C_2H_5$ | 2,3-Cl$_2$C$_6$H$_3$-O- | H | 86 | 75–76 |
| 38 | S | O | $-C_3H_7$-iso | $-CH_3$ | 2,3-Cl$_2$C$_6$H$_3$-O- | H | 85 | 78–80 |
| 39 | S | S | $-C_4H_9$-sec. | $-CH_3$ | $CH_3S-C_6H_4-O-$ | H | 50 | $n_D^{22}$: 1.5610 |
| 40 | S | O | $-C_3H_7$iso | $-CH_3$ | $CH_3S-C_6H_4-O-$ | H | 71 | $n_D^{22}$: 1.5290 |
| 41 | S | O | $-C_2H_5$ | $-C_2H_5$ | $CH_3S-C_6H_4-O-$ | H | 63 | $n_D^{22}$: 1.5360 |
| 42 | S | O | $-C_2H_5$ | $-C_2H_5$ | $C_6H_5-O-$ | H | 71 | $n_D^{22}$: 1.5160 |
| 43 | S | O | $-C_3H_7$-iso | $-CH_3$ | $C_6H_5-O-$ | H | 69 | $n_D^{22}$: 1.5640 |
| 44 | S | O | $-C_2H_5$ | $C_2H_5$ | 2,3,(CH$_3$)$_2$-C$_6$H$_3$-O- | H | 63.9 | 129–136 |
| 45 | S | O | $-CH_3$ | $-C_2H_5$ | 2,3,(CH$_3$)$_2$-C$_6$H$_3$-O- | H | 59.1 | 152–155 |
| 46 | S | O | $-C_2H_5$ | $-CH_3$ | 2,3,(CH$_3$)$_2$-C$_6$H$_3$-O- | H | 51.7 | 124–28 |
| 47 | S | O | $-C_3H_7$-iso | $-CH_3$ | 2,3,(CH$_3$)$_2$-C$_6$H$_3$-O- | H | 37.8 | 132–135 |
| 48 | S | O | $-C_3H_7$-iso | $-CH_3$ | 2-CH$_3$-3-CH$_3$S-C$_6$H$_3$-O- | H | 56.4 | $n_D^{22}$: 1.5341 |
| 49 | S | O | $-C_2H_5$ | $-C_2H_5$ | 2-CH$_3$-3-CH$_3$S-C$_6$H$_3$-O- | H | 43.4 | $n_D^{22}$: 1.5462 |
| 50 | S | O | $-C_2H_5$ | $-C_2H_5$ | NC-C$_6$H$_4$-O- | H | 19.1 | 136–138 |
| 51 | S | O | $-C_3H_7$-iso | $-CH_3$ | NC-C$_6$H$_4$-O- | H | 20 | 104–107 |
| 52 | S | O | $-C_2H_5$ | $-C_2H_5$ | NO$_2$-C$_6$H$_4$-O- | H | 71.9 | 95–98 |

-continued

| Compound No. | X | Y | R₁ | R₂ | R₃ | R₄ | Yield (% of theory) | Physical data (Melting point °C) (refractive index) |
|---|---|---|---|---|---|---|---|---|
| 53 | S | O | —C₃H₇—iso | —CH₃ | NO₂—C₆H₄—O— | H | 68.2 | 97–100 |
| 54 | S | O | —C₂H₅ | —CH₃ | NO—C₆H₄—O— | H | 45 | 91–94 |
| 55 | S | O | —C₂H₅ | —C₂H₅ | CH₃-C₆H₄—O— | H | 80 | $n_D^{23}$: 1.5671 |
| 56 | S | O | —C₃H₇-iso | —CH₃ | CH₃-C₆H₄—O— | H | 80 | 69–70 |
| 57 | S | O | —C₂H₅ | —CH₃ | CH₃-C₆H₄—O— | H | 87 | 68–70 |

Other compounds which can be similarly prepared include:

| Compound No. | X | Y | R₁ | R₂ | R₃ | R₄ |
|---|---|---|---|---|---|---|
| 58 | O | S | —C₂H₅ | —C₂H₅ | C₂H₅—NH—CO—O— | H |
| 59 | O | O | —C₂H₅ | —C₃H₇-n | C₆H₅—CO—O— | H |
| 60 | S | O | —C₂H₅ | —C₂H₅ | C₂H₅—NH—CO—O— | H |
| 61 | O | O | —C₂H₅ | —C₂H₅ | CH₃SO₂—C₆H₄—O— | H |
| 62 | O | O | —C₂H₅ | —C₂H₅ | ClCH₂SO₂—C₆H₄—O— | H |
| 63 | S | O | —C₂H₅ | —C₂H₅ | CH₃O— | H | and the like.

It will be appreciated that the instant specification and examples are set forth by way of illustration and not limitation, and that various modifications and changes may be made without departing from the spirit and scope of the present invention.

What we claim is:

1. An O-[6-substituted-pyridazin(3)yl]-(thiono) (thiol-)alkanephosphonic acid ester of the formula

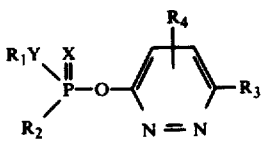

in which
X and Y each independently is oxygen or sulfur,
$R_1$ is alkyl with 1 to 6 carbon atoms,
$R_2$ is alkyl with 1 to 4 carbon atoms,
$R_3$ is alkoxy with 1 to 4 carbon atoms, alkynyloxy with 2 to 5 carbon atoms, alkylsulfonyloxy with 1 to 3 carbon atoms, monoalkylcarbamoyloxy with 1 to 3 carbon atoms, halogen, benzyloxy, benzoyloxy, phenoxy, or phenoxy carrying up to three substituents selected from halogen, nitro, cyano, —SO₂CH₃, —SO₂CH₂Cl, and alkyl, halogenalkyl or alkylthio, each with up to 3 carbon atoms, and
$R_4$ is hydrogen or alkyl with 1 to 3 carbon atoms.

2. An ester according to claim 1, in which
X is sulfur,
Y is oxygen,
$R_1$ is alkyl with 1 to 5 carbon atoms,
$R_2$ is alkyl with 1 to 3 carbon atoms,
$R_3$ is alkoxy with 1 to 3 carbon atoms, alkynyloxy with 3 or 4 carbon atoms, chlorine, bromine methylsulfonyloxy, ethylsulfonyloxy, N-methylcarbamoyloxy, N-ethylcarbamoyloxy, benzoyloxy, benzyloxy, phenyloxy, or phenyloxy carrying up to three substituents selected from chlorine, nitro, cyano, methyl, ethyl, methylthio, ethylthio and trifluoromethyl, and
$R_4$ is hydrogen, methyl or ethyl.

3. The compound according to claim 1, wherein such compound is O-isobutyl-O-[6-chloro-pyridazin(3)yl]-thionoethanephosphonic acid ester of the formula

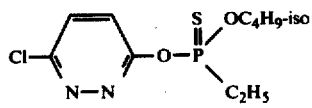

4. The compound according to claim 1, wherein such compound is O-isopropyl-O-[6-ethoxy-pyridazin(3)yl]-thionoethanephosphonic acid ester of the formula

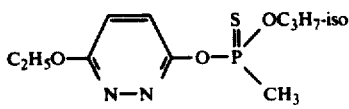

5. The compound according to claim 1, wherein such compound is O-methyl-O-[6-ethoxy-pyridazin(3)yl]-thionoethanephosphonic acid ester of the formula

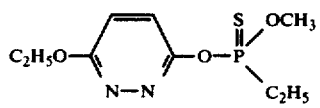

6. The compound according to claim 1, wherein such compound is O-methyl-O-[6-methylsulfonyloxy-pyridazin(3)yl]-thionoethanephosphonic acid ester of the formula

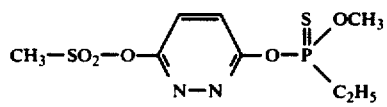

7. The compound according to claim 1, wherein such compound is O-isopropyl-O-[6-(2',4'-dichlorophenoxy)-pyridazin(3)yl]-thionomethanephosphonic acid ester of the formula

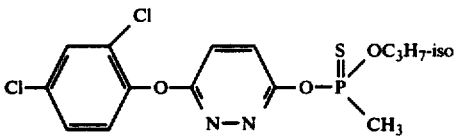

8. An insecticidal, acaricidal, nematicidal or fungicidal composition containing as active ingredient an insecticidally, acaricidally, nematicidally or fungicidally effective amount of a compound according to claim 1 in admixture with at least 5% by weight of the composition of a conventional inert pesticide diluent and optionally also a known compatible plant protection agent.

9. A method of combating insects, acarids or nematodes which comprises applying to the insects, acarids or nematodes, or to a habitat thereof, an insecticidally, acaricidally or nematicidally effective amount of a compound according to claim 1.

10. The method according to claim 9 in which said compound is O-isobutyl-O-[6-chloro-pyridazin(3)yl]-thionoethanephosphonic acid ester, O-isopropyl-O-[6-ethoxy-pyridazin(3)yl]-thionomethanephosphonic acid ester, O-methyl-O-[6-ethoxy-pyridazin(3)yl]-thionomethanephosphonic acid ester, O-methyl-O-[6-methylsulfonyloxy-pyridazin(3)yl]-thionoethanephosphonic acid ester or O-isopropyl-O-[6-(2',4'-dichlorophenoxy)-pyridazin(3)yl]-thionomethanephosphonic acid ester.

* * * * *